US009662096B2

(12) United States Patent
Kindt et al.

(10) Patent No.: US 9,662,096 B2
(45) Date of Patent: May 30, 2017

(54) DEVICES AND KITS FOR COLLECTION, STORAGE AND ANALYSIS OF SAMPLES AND METHODS OF PRODUCTION AND USE THEREOF

(71) Applicant: Diomics Corporation, San Diego, CA (US)

(72) Inventors: Thomas J. Kindt, Phoenix, AZ (US); John F. Steel, La Jolla, CA (US); Beverly L. Wolgast, San Diego, CA (US); Ryan Lamer, San Diego, CA (US)

(73) Assignee: DIOMICS CORPORATION, San Diego, CA (US)

( * ) Notice: Subject to any disclaimer, the term of this patent is extended or adjusted under 35 U.S.C. 154(b) by 39 days.

(21) Appl. No.: 14/700,539

(22) Filed: Apr. 30, 2015

(65) Prior Publication Data
US 2015/0315564 A1    Nov. 5, 2015

Related U.S. Application Data

(60) Provisional application No. 61/987,143, filed on May 1, 2014.

(51) Int. Cl.
*A61B 10/00*     (2006.01)
*A61B 10/02*     (2006.01)
(Continued)

(52) U.S. Cl.
CPC .......... *A61B 10/02* (2013.01); *A61B 10/0038* (2013.01); *A61B 10/0045* (2013.01);
(Continued)

(58) Field of Classification Search
CPC ............ A61B 10/0038; A61B 10/0045; A61B 10/0051; A61B 10/0058; A61B 10/0064;
(Continued)

(56) References Cited

U.S. PATENT DOCUMENTS

| 4,455,206 A | 6/1984 | Funabashi et al. |
|---|---|---|
| 5,129,402 A | 7/1992 | Koll et al. |

(Continued)

FOREIGN PATENT DOCUMENTS

| EP | 2249140 | 11/2010 |
|---|---|---|
| JP | 556061 | 2/1980 |

(Continued)

OTHER PUBLICATIONS

International Search Report mailed on Jul. 29, 2015 in PCT/2015/028458.

(Continued)

*Primary Examiner* — Devin Henson
(74) *Attorney, Agent, or Firm* — Fox Rothschild LLP

(57) ABSTRACT

Collection devices, kits and methods related to sample collection and analysis can be used to collect and store samples (e.g., biological samples) from a variety of sources and optionally, for analysis of such samples (e.g., forensics analysis, medical diagnostics, etc.). Methods of production and use thereof are described herein. A device for collecting a sample (e.g., a sample including nucleic acid) includes an outer protective housing and a collection tip operably coupled to a carrier. The collection tip includes a hydrophilic and at least partially soluble material (e.g., hydrophilic and at least partially soluble polycaprolactone (PCL)) and is movable (e.g., retractable) from a first protected position within the outer protective housing to a second collecting position outside the outer protective housing.

21 Claims, 4 Drawing Sheets

(51) Int. Cl.
| | |
|---|---|
| *C12N 15/10* | (2006.01) |
| *B65D 85/00* | (2006.01) |
| *B65D 81/26* | (2006.01) |
| *A61B 19/02* | (2006.01) |
| *A61B 50/00* | (2016.01) |
| *G01N 1/02* | (2006.01) |
| *A61B 90/98* | (2016.01) |
| *G01N 1/00* | (2006.01) |
| *A61B 90/90* | (2016.01) |
| *B01L 3/00* | (2006.01) |

(52) U.S. Cl.
CPC .......... *A61B 19/0262* (2013.01); *A61B 50/00* (2016.02); *B65D 81/266* (2013.01); *B65D 85/70* (2013.01); *C12N 15/1006* (2013.01); *A61B 10/0051* (2013.01); *A61B 10/0058* (2013.01); *A61B 10/0064* (2013.01); *A61B 90/90* (2016.02); *A61B 90/98* (2016.02); *A61B 2010/0074* (2013.01); *A61B 2010/0216* (2013.01); *B01L 3/5029* (2013.01); *G01N 2001/007* (2013.01); *G01N 2001/028* (2013.01)

(58) Field of Classification Search
CPC .... A61B 2010/0074; A61B 2010/0216; A61B 90/90; A61B 90/98; B65D 81/266; B01L 3/5029; G01N 2001/007; G01N 2001/028; C12N 15/1006
See application file for complete search history.

(56) References Cited

U.S. PATENT DOCUMENTS

| | | | |
|---|---|---|---|
| 5,874,045 | A | 2/1999 | Chisum |
| 5,916,802 | A | 6/1999 | Andreotti |
| 6,103,255 | A | 8/2000 | Levene et al. |
| 6,268,222 | B1 | 7/2001 | Chandler et al. |
| 7,615,373 | B2 | 11/2009 | Simpson et al. |
| 7,790,865 | B1 | 9/2010 | Heath et al. |
| 7,927,548 | B2 | 4/2011 | Slowey et al. |
| 7,978,074 | B2 | 7/2011 | Nikitin et al. |
| 8,049,623 | B2 | 11/2011 | Morris et al. |
| 8,586,345 | B2 | 11/2013 | Simpson et al. |
| 8,685,747 | B2 | 4/2014 | Zenhausern |
| 8,696,595 | B2 | 4/2014 | Sangha |
| 8,759,075 | B2 | 6/2014 | Morhet et al. |
| 9,200,321 | B2 * | 12/2015 | Caragine ............... A61B 10/00 |
| 2003/0129738 | A1 | 7/2003 | Sorenson et al. |
| 2003/0193118 | A1 | 10/2003 | Bango et al. |
| 2007/0167900 | A1 | 7/2007 | Kanjilal et al. |
| 2008/0299164 | A1 | 12/2008 | Trollsas |
| 2009/0156962 | A1 | 6/2009 | Yong et al. |
| 2010/0226960 | A1 | 9/2010 | Chudzik et al. |
| 2010/0274155 | A1 | 10/2010 | Battrell et al. |
| 2010/0317051 | A1 | 12/2010 | Hanselle et al. |
| 2011/0001609 | A1 | 1/2011 | Oldham et al. |
| 2011/0004122 | A1 * | 1/2011 | Sangha ............... A61B 10/0045 600/572 |
| 2011/0008771 | A1 | 1/2011 | Hanselle et al. |
| 2012/0122091 | A1 * | 5/2012 | Vom ............... A61B 10/0291 435/6.11 |
| 2012/0149021 | A1 | 6/2012 | Yung et al. |
| 2012/0329081 | A1 * | 12/2012 | Bennion ............... B01L 3/5023 435/8 |
| 2014/0073988 | A1 | 3/2014 | McSherry |
| 2014/0171828 | A1 * | 6/2014 | Blitzer ............... A61B 10/02 600/569 |

FOREIGN PATENT DOCUMENTS

| | | |
|---|---|---|
| WO | 9803267 | 1/1998 |
| WO | 2006089297 | 8/2006 |
| WO | 2008157422 | 12/2008 |
| WO | 2009012808 | 1/2009 |
| WO | 2010123462 | 10/2010 |
| WO | 2011094745 | 8/2011 |
| WO | 2012024407 | 2/2012 |
| WO | 2014011536 | 4/2014 |

OTHER PUBLICATIONS

European Search Report mailed on Mar. 13, 2015 in Application No. EP 13 81 6496. (11 pages).
International Search Report and the Written Opinion of the ISA mailed on Dec. 20, 2013 in international Application No. PCT/US2013/049560. (17 pages).
Armani et al., "Microfabrication technology for polycaprolactone, a biodegradable polymer", J. Micromech. Microeng. PII: S0960-1317(00)08138-9, 10 (20000), 80-84.
B. Alp et al., "Crystallization Control of Polycaprolactone (PCL) with Inorganic and Organic Additives", 4 Pgs.
Naidoo et al., "An emulsion preparation for novel micro-porous polymeric hemi-shells", Science Direct, Material Letters 62, 2008, pp. 252-254.
Perego et al., "Functionalization of poly-L-lactic-co-e-caprolactone: effects of surface modification on endothelial cell proliferation and hemocompatibility", Improved endothelial adhesion for small diameter graft, J. Biomater. Sci. Polymer Edn, vol. 14, No. 10, 2003, pp. 1057-1075.
Pok et al., "In vitro characterization of polycaprolactone matrices generated in aqueous media", Acta Biomater, (Mar. 2010) 6(3): 1061-1068. doi: 10.1016/j.actbio.2009.08.00.
Spiess et al., "Trehalose is a potent PCR enhancer: Lowering of DNA metlting temperature and thermal stabilization of Taq Polymerase by the disaccharide trehalose", Clin Chem (Jul. 2004) 50(7): 1256-1259.
Thapa et al., "Polymers with nando-dimensional surface features enhance bladder smooth muscle cell adhesion", Enhancement of Bladder SMC Adhesion, Wiley Periodicals, Inc., 2003, pp. 1374-1383.
Woodruff et al., "The return of a forgotten polymer—Polycaprolactone in the 21st Century", Progress in Polymer Science, Apr. 2, 2010, pp. 1-40.
Zhang et al., "The encapuslation and intracellular delivery of trehalose using a thermally responsive nanocapsule", Nanotechnology (2009) 20 (275101): 1-14.

* cited by examiner

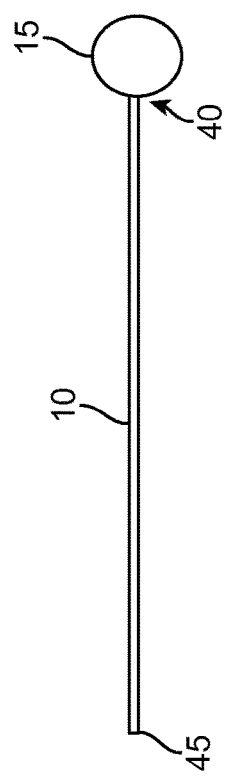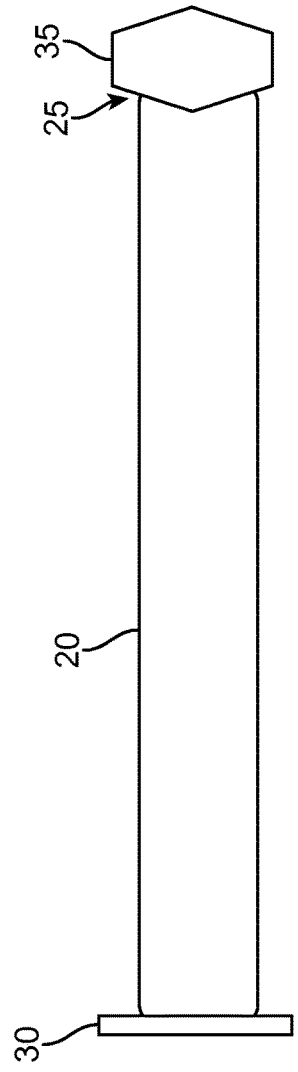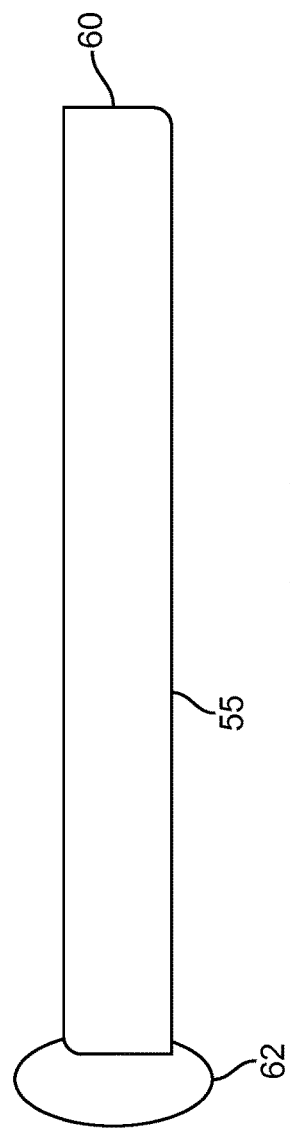

DEVICES AND KITS FOR COLLECTION, STORAGE AND ANALYSIS OF SAMPLES AND METHODS OF PRODUCTION AND USE THEREOF

CROSS-REFERENCE TO RELATED APPLICATIONS

This application claims the benefit of U.S. Provisional application 61/987,143, filed May 1, 2014, hereby incorporated by reference in its entirety.

FIELD OF THE INVENTION

Devices, kits and methods related to sample collection, storage and analysis that include hydrophilic and at least partially soluble collection tips are described herein.

BACKGROUND

Forensic DNA analysis provides one of the most definitive proofs of human identification allowed by modern technology. Success of deoxyribonucleic acid (DNA) typing is related to the quality and quantity of the DNA recovered for analysis. Most devices currently employed by law enforcement for crime scene sample collection (e.g. cotton or nylon swabs) are inefficient in DNA release leading to less than desirable recovery of DNA and possible poor analysis. A superior technology that allows capturing greater amounts of biological materials from crime scenes and is engineered to release the captured DNA in a manner conducive to yield high quantities and quality, if present in a sample, would be of substantial benefit to law enforcement in developing more investigative leads, solving more crimes, excluding individuals not associated with limited quantity samples, and ultimately result in significant savings for investigators and the laboratory. In conjunction with optimizing sample collection and DNA release, providing more sensitive analytical methods can aid in current difficult to analyze sample types, e.g., touch DNA samples, remains from mass disasters and missing persons identifications.

SUMMARY

Described herein are devices for collecting a sample, methods of collecting a sample, and kits for collecting a sample. These devices, kits and methods can also be used for storing and analyzing the collected sample. A device for collecting a sample (e.g., a sample including nucleic acid) includes an outer protective housing and a collection tip operably coupled to a carrier. The collection tip includes a hydrophilic and at least partially soluble material (e.g., hydrophilic and at least partially soluble polycaprolactone (PCL)) and is movable (e.g., retractable) from a first protected position within the outer protective housing to a second collecting position outside the outer protective housing. The outer protective housing can have a removable cap attached thereto, or can have a cap that is operably coupled to the outer protective housing. In some embodiments, the cap includes a desiccant for drying the sample that is collected. In some embodiments, the collection tip is easily separated (mechanically separated) from the carrier or a portion of the carrier for ease of using the collection tip with acquired sample in extraction processes. Methods of collecting a sample (e.g., a forensics sample, medical sample, etc.) include contacting the sample with a device as described herein for collecting a sample under conditions such that at least a portion of the sample reversibly adheres to the collection tip. These methods can further include analyzing the sample as described in more detail below.

These collection devices include retractable collection tip devices and are used for the efficient collection and storage, in a preserved state, of samples such as biologic samples and are capable of releasing the majority of various biochemical analytes such as protein, genomic DNA, cDNA, RNA or mitochondrial DNA from the collected sample under appropriate extraction conditions. The collection tip of the device lends itself to efficient pick-up of biologic samples and extraction of desired analytes with little or no retention of the desired analyte in the collection material. In a typical device, Diomat™ (Diomics Corp., San Diego, Calif.) material is used for the collection tip, as it has shown superiority in collecting biologic samples and the subsequent release of nucleic acids (e.g., DNA) from them. Construction and use of Diomat™ (Diomics Corp., San Diego, Calif.) is described in detail in U.S. Pat. No. 8,759,075, which is incorporated by reference herein. Other suitable materials for the collection tip are also encompassed by the devices, methods and kits described herein, and are described in more detail below.

Unless otherwise defined, all technical terms used herein have the same meaning as commonly understood by one of ordinary skill in the art to which this invention belongs.

As used herein, the term "analyte" means any substance that is measured, analyzed or detected.

By the term "biologic analyte" is meant any molecule, compound, protein, nucleic acid, small molecule, spore, or organism (a bacterium, bacterial spore, virus, mold, fungus, parasite) or any component of an organism. "Biologic analytes" include nucleic acids (e.g., DNA, methylated DNA), peptides, proteins, lipids, and carbohydrates, particularly those relevant to disease processes and/or forensic applications. A "biologic analyte" is typically present within a sample.

The term "sample" is used herein in its broadest sense. A sample that is collected using a device, kit or method as described herein is any material to be analyzed. Examples include nucleic acids, cells, tissues, or bodily fluids such as saliva, blood, urine, semen, mucus, lymphatic fluid, cerebrospinal fluid, or amniotic fluid, or other biological samples, such as fingerprints, buccal swabs, mouthwashes, stool, tissue culture cells, tissues slices, biopsy aspiration, etc.

As used herein, "protein" and "polypeptide" are used synonymously to mean any peptide-linked chain of amino acids, regardless of length or post-translational modification, e.g., glycosylation or phosphorylation.

By the term "gene" is meant a nucleic acid molecule that codes for a particular protein, or in certain cases, a functional or structural RNA molecule.

As used herein the terms "nucleic acid" and "nucleic acid molecule" are intended to encompass single- and double-stranded DNA (deoxyribonucleic acid) and RNA (ribonucleic acid) (and forms thereof that can be partially single-stranded or partially double-stranded), as well as any and all forms of alternative nucleic acid containing modified bases, sugars, and backbones. Examples of DNA include eukaryotic or prokaryotic genomic DNA, oligonucleotides, mitochondrial DNA, cDNA, specific gene sequences, short tandem repeats (STRs), bacterial plasmids, bacteriophage DNA etc. The terms "nucleic acid" and "nucleic acid molecule" will be understood to include, but not be limited to DNA, RNA, cDNA, aptamers, peptide nucleic acids ("PNA"), 2'-5' DNA (a synthetic material with a shortened backbone that has a base-spacing that matches the A conformation of DNA; 2'-5' DNA will not normally hybridize with DNA in the B form, but it will hybridize readily with RNA), and locked nucleic acids ("LNA"). Nucleic acid analogues include known analogues of natural nucleotides that have similar or improved binding, hybridization of base-pairing properties.

The terms "nucleic acid template" or "nucleic acid templates," as used herein, refer to a nucleic acid or nucleic acids that serve as starting material for the synthesis of a short tandem repeat (STR) profile. Nucleic acid template(s) may be double stranded or single stranded. The templates can include DNA from one or more whole genomes of an individual, partial genomes of an individual, or previously amplified products from DNA of the individual and can include mixtures of whole and partial genomes from two or more individuals. The genomes to be analyzed may be derived from humans, from other mammalian species, or from mixtures.

The term "polymorphic site" as used herein refers to at least one nucleotide site in a DNA sequence that differs among certain individuals of a given species, such as humans.

The terms "locus" and "loci" (plural), as used herein, mean one or more specific positions within the whole or partial genomes of a given species, as defined herein.

The terms "STR locus" and "STR loci," as used herein, mean a nucleotide sequence consisting of a repeating pattern of two or more nucleotides at a given locus of a target nucleic acid. The repeating pattern can range in length from about 2 to about 10 base pairs (bp), and is typically in the non-coding intron region. The repeating pattern may contain intervening sequences that do not correspond to the repeat unit, or may contain more than one repeating pattern.

The terms "STR allele" or "allele," as used herein, refer to a form of an STR locus found in the genome of an individual. A given STR locus may be heterozygous, meaning that the two alleles (one inherited from each biological parent) are of different lengths and base pair composition, or may be homozygous, meaning that both alleles are of identical length (and usually but not always base pair composition). Rarely, an individual may have three or more alleles for a given STR locus. Occasionally, an individual's alleles at a given STR locus may differ from his or her parents due to one or more mutations.

By the phrase "modified PCL" is meant any PCL that has been treated or modified such that the hydrophilicity of the PCL is increased and/or such that one or more surface features of the PCL have been modified (e.g., chemical and/or physical modifications). Examples of surface features include texture (e.g., roughness, smoothness), holes, dimples, channels, protrusions and other irregularities. Any suitable treatment methods, including chemical or physical treatments, for increasing hydrophilicity and/or modifying surface features of PCL can be used. For example, PCL can be subjected to (treated with) a base (e.g. having a pH above 8). Examples of bases include $NaHCO_3$ and NaOH.

As used herein, the phrase "at least partially soluble and hydrophilic PCL" means PCL (which is inherently hydrophobic) that has been treated in some manner to make it hydrophilic (absorb water) and to become soluble in an analyte extraction reagent(s) (e.g., biological analyte extraction reagents such as DNA extraction reagents, detergent solutions, etc.). By "at least partially soluble" is meant at least 50% (e.g., 50%, 55%, 60%, 65%, 70%, 75%, 80%, 85%, 90%, 95%, 96%, 97%, 98%, 99%, 99.5%, 100%) of the weight of the solid collection material. "At least partially soluble and hydrophilic PCL" is an example of a modified PCL. Diomat™ is a commercially available source of modified PCL that is hydrophilic and at least partially soluble and that can be used in the devices, kits and methods described herein. Construction and use of Diomat™ is described in U.S. Pat. No. 8,759,075, which is incorporated herein by reference.

By the term "biologic analyte extraction reagent" is meant any reagent (e.g., solution) that can be used to extract or separate a biologic analyte from a sample. If the biologic analyte is a nucleic acid from a cell or organism, the extraction reagent is any reagent (e.g., nucleic acid extraction reagent or solution) that can be used to separate the nucleic acid (e.g., DNA, RNA, cDNA, mitochondrial DNA, genomic DNA) from the cell (and, e.g., from the remaining sample) or organism. An extraction reagent used for nucleic acid extraction can be, for example, a solution containing one or more of: a detergent to disrupt cell and nuclear membranes, a proteolytic enzyme(s) to degrade proteins, an agent to inhibit nuclease activity, a buffering compound to maintain neutral pH, and chaotropic salts to facilitate disaggregation of molecular complexes. If protein assays are to be used for analyzing a biologic analyte, extraction solutions will not include proteolytic enzymes and may utilize organic solvents.

By the phrase "nucleic acid extraction reagent" is meant any reagent (e.g., solution) that can be used to obtain a nucleic acid (e.g., DNA) from biological samples and materials such as cells, tissues, bodily fluids, microorganisms, etc. A nucleic acid extraction reagent can be, for example, a solution containing one or more of: a detergent to disrupt cell and nuclear membranes, a proteolytic enzyme(s) to degrade proteins, an agent to inhibit nuclease activity, a buffering compound to maintain neutral pH, and chaotropic salts to facilitate disaggregation of molecular complexes.

As used herein, the term "carrier" refers to any structure, member or implement that can be operably coupled to a collection tip as described herein. A carrier as described herein assists man or machine in exposing the collection tip (e.g., modified PCL) to a sample (e.g., a biologic analyte such as nucleic acid), and subsequent processing, e.g., hand held or "machine-held." A carrier can be, for example, an elongated shaft. Another example of a carrier is an elongated shaft and a structure (e.g. a plunger or plunger-like device) having an internal elongated opening for receiving the elongated shaft. Carriers can be made of any suitable materials, and are typically made of rigid and/or semi-rigid materials. Examples of such materials include wood, plastic, glass, rubber, and polymers.

As used herein, the term "copolymerized" refers to using two or more monomeric units to form a polymer with inclusion of both in some random (e.g., AABABB-BAABAAABBBBA) or defined order (such as, e.g., AAABAAABAAAB or ABABABAB or ABAABAABAABAABAABA). For example, when referring to PCL that is copolymerized with at least one agent such as, e.g., L-lactic acid, the copolymer formed is a poly caprolactide called poly-L-lactic-co-ε-caprolactone.

By the term "neutralizing agent" is meant any reagent (e.g., a solution, liquid, etc.) that when contacted with PCL, for example, brings the pH of the PCL to a neutral pH. Nonlimiting examples of neutralizing agents include water and acidic solutions.

The terms "patient," "subject" and "individual" are used interchangeably herein, and mean a mammalian (e.g., human, rodent, non-human primates, canine, bovine, ovine, equine, feline, etc.) subject to obtain a biologic sample from. In forensics embodiments, a subject or individual may be a potential or suspected perpetrator of a crime, for example. A subject or individual may be one who has left evidence of having been in an area (e.g., a "donor").

The phrases "isolated" or biologically pure" refer to material which is substantially or essentially free from components which normally accompany it as found in its native state.

As used herein, the phrase "surface of forensic interest" means any surface area of interest to law enforcement personnel because of a crime, or suspected crime in that area. For example, a weapon or any object handled by a potential perpetrator of crime may include a surface of forensic interest and used to obtain fingerprints (e.g., DNA from cells shed by fingerprints) or DNA to identify the person of interest. A gun trigger or recovered stolen object may include a surface to be scanned for evidence.

The phrase "a trace sample's donor" as used herein means an individual (the donor) who has left evidence of having been in an area; if the evidentiary sample is very small it is considered a trace sample.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Accordingly, described herein is a device for collecting a sample (collection device). The device includes an outer protective housing and a collection tip operably coupled to a carrier, the collection tip including a hydrophilic and at least partially soluble material and being movable from a first protected position within the outer protective housing to a second collecting position outside the outer protective housing. In the device, the outer protective housing typically includes a first end a second end, and the device can further include a removable cap attached to the first end of the outer protective housing when the collector tip is in the first protected position, or a cap that is operably coupled to the outer protective housing (e.g., such that it can be moved or manipulated to allow the carrier and collection tip to move between protected and collecting positions without the cap being completely separated from the collection device). In the device, the removable cap or the cap that is operably coupled to the outer protective housing can include a desiccant (drying agent or material). In one embodiment, the hydrophilic and at least partially soluble material is hydrophilic and at least partially soluble PCL. Typically, the PCL has been treated with a base having a pH greater than 8 and a neutralizing agent for increasing hydrophilicity and optionally is copolymerized with an acrylamide or a polyester other than PCL. The device can further include an identifying label or a radio-frequency identification (RFID) tag, or a combination thereof. In a typical embodiment, the sample includes nucleic acid and at least a portion of the collection tip solubilizes when exposed to a nucleic acid extraction reagent.

In one embodiment of the collection device, the carrier includes an elongated shaft having a first end and a second end, and the collection tip is attached to the first end such that the collection tip, and optionally an adjacent portion of the first end of the elongated shaft, is mechanically separable from the carrier. In an embodiment in which the carrier includes an elongated shaft, the carrier can include a plunger (or plunger-like structure or apparatus) having an internal elongated opening for receiving the elongated shaft. In this embodiment, the outer protective housing and the carrier can include a syringe, and the collector tip can be movable from a first protected position within the outer protective housing to a second collecting position outside the outer protective housing when pressure is applied to the plunger (or plunger-like structure or apparatus). In such an embodiment, the outer protective housing can include a first end a second end, and such a device can further include a removable cap attached to the first end of the outer protective housing when the collector tip is in the first protected position, or a cap that is operably coupled to the outer protective housing. The removable cap or the cap that is operably coupled to the outer protective housing can include a desiccant.

Also described herein is a kit for collecting at least one sample. A typical kit includes: a plurality of devices for collecting at least one sample (collection devices) that includes nucleic acid, each of the devices including an outer protective housing and a collection tip operably coupled to a carrier, the collection tip including a hydrophilic and at least partially soluble material and being movable from a first protected position within the outer protective housing to a second collecting position outside the outer protective housing; a nucleic acid extraction reagent; instructions for use; and packaging. In a kit, each of the devices can include an identifying label or a radio-frequency identification (RFID) tag, or a combination thereof. The packaging can include a desiccant. For example, each of the devices can be individually packaged and each package can include a desiccant.

Further described herein is a method of collecting at least one sample. A typical method includes contacting the at least one sample with a device for collecting a sample, the device including an outer protective housing and a collection tip operably coupled to a carrier, the collection tip including a hydrophilic and at least partially soluble material and being movable from a first protected position within the outer protective housing to a second collecting position outside the outer protective housing, under conditions such that at least a portion of the at least one sample reversibly adheres to the collection tip. The at least one sample can include nucleic acid, and the method can further include contacting the collection tip and adhered at least a portion of the at least one sample with a nucleic acid extraction agent resulting in separation of about 51% to about 95% of the nucleic acid from the collection tip. The sample can be a forensics sample, a medical diagnostics sample, etc. In some embodiments, the sample is from a human. In some embodiments, multiple samples (e.g., human samples) are collected and optionally, analyzed. The collection, and optionally analysis, of multiple samples can be done simultaneously, in parallel, or in a serial manner. The devices, methods and kits can be used for high-throughput collection and analysis of samples (e.g., human samples).

Other features will become more apparent to persons having ordinary skill in the art to which the package pertains and from the following description and claims. Although devices, kits, and methods similar or equivalent to those described herein can be used in the practice or testing of the present invention, suitable devices, kits, and methods are described below. All publications, patent applications, and patents mentioned herein are incorporated by reference in their entirety. In the case of conflict, the present specification, including definitions, will control. The particular embodiments discussed below are illustrative only and not intended to be limiting.

BRIEF DESCRIPTION OF THE DRAWINGS

The above and other aspects, features and advantages of the present embodiments will be more apparent from the following more particular description thereof, presented in conjunction with the following figures.

FIGS. 1A-1C show one embodiment of a collection device. FIG. 1A is a side elevation of a carrier and collection tip of a collection device. FIG. 1B is a side elevation of an outer protective housing having a cap attached thereto. FIG. 1C is a side elevation of a structure (e.g., a plunger or plunger-like device) having an internal elongated opening for receiving an elongated shaft.

FIG. 2A is a side elevation of a plunger as shown in FIG. 1C and a carrier and collection tip as shown in FIG. 1A. In FIG. 2A, the carrier includes an elongated shaft having a first end and a second end, and the collection tip is attached to the first end such that the collection tip, and optionally an adjacent portion of the first end of the elongated shaft, is mechanically separable from the rest of the elongated shaft. The area of the elongated shaft that is separable is sometimes referred to as a "breakaway point" as it can be broken or snapped off, severed, etc. FIG. 2B is a side elevation partially in cross section of an assembled collection device having the structure (e.g., plunger or plunger-like device), elongated shaft and collection tip of FIG. 2A within an outer protective housing that has a removable cap attached thereto. In FIG. 2B, the collection tip is in a first protected position within the outer protective housing which has a removable cap attached thereto. FIG. 2C is a side elevation partially in cross section of the assembled collection device of FIG. 2B in which the removable cap has been removed and the collection tip and most or all of the elongated shaft are in a second collecting position outside the outer protective housing.

DETAILED DESCRIPTION

Figure 2A:
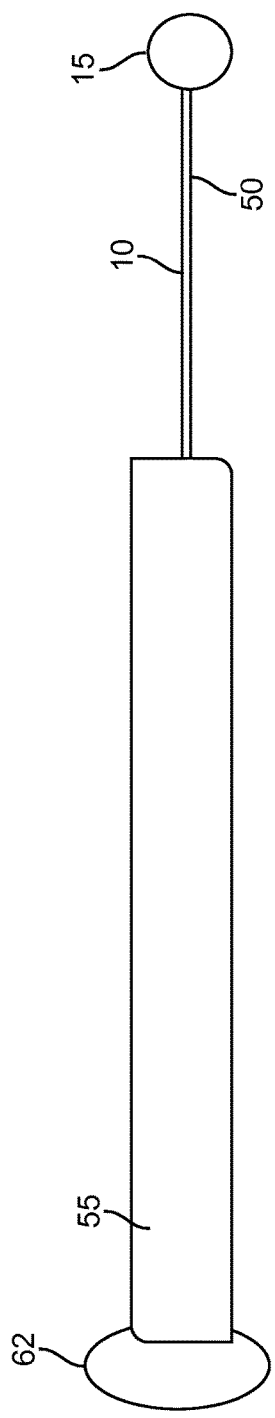
FIGS. 2A-2C show assembly and use of one embodiment of a collection device.

The following description is not to be taken in a limiting sense, but is made merely for the purpose of describing the general principles of exemplary embodiments. The scope of the embodiments should be determined with reference to the claims. The collection devices described herein (e.g., retractable tip collection devices) provide more efficient recovery of analytes (e.g., biologic analytes such as nucleic acids, e.g., DNA) from, for example, a variety of body fluids and stains, and particularly low quantity samples and provide for the preservation of these samples in the same device until extraction of analytes (e.g., target analytes such as nucleic acid) can be accomplished. The collection devices may be used to obtain samples (e.g., biologic samples) for applications such as forensics and additionally diagnostics (medical diagnostics), where biologic samples (e.g., blood, urine saliva, mucus or other body component or fluid) may be collected from individuals (e.g., patients) for the purpose of detecting disease, measuring its severity, and/or monitoring effects of treatment (treatment efficacy, drug efficacy). In a diagnostic embodiment, the sample(s) obtained and analyte(s) measured may depend on the specific disease or condition to be detected or monitored. In such embodiments, individuals tested may have undetected disease or may be tested to monitor progress of disease or response to treatment.

Collection Devices for Collecting, Storing and Optionally, Analyzing, Samples

A device for collecting a sample as described herein includes an outer protective housing and a collection tip operably coupled to an elongated shaft. The carrier can be any suitable shape or structure for supporting and/or coupling to a collection tip, e.g., a post, stick, handle, member, rod, etc. A carrier can be, for example, an elongated shaft. Another example of a carrier is an elongated shaft and a structure (e.g. a plunger or plunger-like device) having an internal elongated opening for receiving the elongated shaft. In the embodiments of FIGS. 1-3, the carrier is an elongated shaft. A collection device as described herein includes a collection tip operably coupled to a carrier, and an outer protective housing. The outer protective housing can have any suitable shape and dimensions for receiving or housing the collection tip operably coupled to a carrier. The collection tip includes or is a hydrophilic and at least partially soluble material to which sample reversibly adheres. The collection tip is movable from a first protected position within the outer protective housing to a second collecting position outside the outer protective housing. The outer protective housing can have a first end a second end, and the device can further include a removable cap attached to one of the two ends of the outer protective housing (e.g., the first end of the outer protective housing) when the collector tip is in the first protected position, or a cap that is operably coupled to the outer protective housing such that it can be moved or manipulated to allow the carrier and collection tip to move between protected and collecting positions without the cap being completely separated from the collection device. This embodiment may be particularly useful for avoiding dropping and/or losing the cap. In some embodiments, the removable cap or the cap that is operably coupled to the outer protective housing includes a desiccant for drying the sample.

FIG. 1 shows the components of one embodiment of a collection device as described herein. Referring to FIG. 1A, a collection tip 15 operably coupled to an elongated shaft 10 is shown. The elongated shaft 10 has a first end 40 and a second end 45. The collection tip 15 is attached to the first end 40 of the elongated shaft 10. Although the collection tip 15 is shown as a sphere in FIG. 1B, the collection tip 15 can take any shape. In a typical embodiment, the collection tip 15 is or includes modified PCL that is hydrophilic and at least partially soluble. The elongated shaft 10 is a semi-rigid or rigid material, for example, wood, plastic, glass, rubber, and polymers. However, the elongated shaft 10 (and any carrier described herein) can be constructed of any other suitable material or combination of materials.

The outer protective housing can be, for example, a hollow tube or cylinder, a case, container, chamber, rectangular prism, etc. The outer protective housing can be made of any suitable material, e.g., plastic, glass, rubber, a polymer, etc. In FIG. 1B, one embodiment of an outer protective housing 20 is shown. The outer protective housing 20 has a first end 25 and a second end 30. A removable cap 35 is shown attached to the first end 25 of the outer protective housing 20. The collection tip 15 operably coupled to an elongated shaft 10 is movable from a first protected position within the outer protective housing 20 to a second collecting position outside the outer protective housing 20. The extent to which the collection tip extends outside the outer protective housing when in the second collecting position can vary, and may depend on the particular embodiment of collection device. In some embodiments, the collection tip 15 may extend just beyond the first end 25 of the outer protective housing 20, while in other embodiments, the collection tip 15 may extend further beyond the first end 25 of the outer protective housing 20 and thus further outside the outer protective housing 20. A typical collection device as described herein may be referred to as a retractable collection device due to the movement of the collection tip between protected and collecting positions. In the embodiment shown in FIG. 1B, the cap is a removable cap 35. The removable cap 35 can be attached to the outer protective housing 20 for enclosing and protecting collection tip 15 by any suitable means. For example, it can be snapped, fastened, screwed or threaded on, e.g., by any means allowing facile removal for use and resealing for storage of acquired sample. In alternative embodiments, the cap is operably coupled to the outer protective housing 20 such that it can be moved or manipulated to allow the collection tip 15 to move between protected and collecting positions without the cap being completely separated from the collection device. This embodiment may be particularly useful for avoiding dropping and/or losing the cap. In an embodiment in which the collection device includes such a cap that is operably coupled to the outer protective housing, the cap may be permanently attached to the outer protective housing 20 by any suitable means, e.g., by a cord or elastic band that allows it to be closed or opened with ease. There may also be an attachment site to secure the cap to the outer protective housing 20 for use when the collection device is opened (e.g., when the collection tip is in a collecting position), for example, a magnet paired with a ferromagnetic strip, velcro on both the cap and the outer protective housing 20, etc. In any of these embodiments, the cap may be made of any suitable material, and would typically be, for example, plastic, glass, polymer, rubber, synthetic material, etc.

In FIG. 1C, a structure 55 (e.g., a plunger) that has an internal elongated opening 60 at one end for receiving the elongated shaft 10 and collection tip 15 is shown. The structure 55 (e.g., plunger) provides for movement of the elongated shaft 10 and collection tip 15 between protected and collecting positions. In this embodiment, structure 55 is a plunger or plunger-like device. Structure 55 can be any suitable shape and dimensions such that it can be positioned and movable within the outer protective housing 20. Structure 55 can be made of any suitable material, e.g., rubber, plastic, glass, synthetic material, a polymer, etc. In the embodiment shown in FIG. 1C, structure 55 has a handle or knob 62 at the end opposite of the end having the internal elongated opening 60.

Figure 2B:
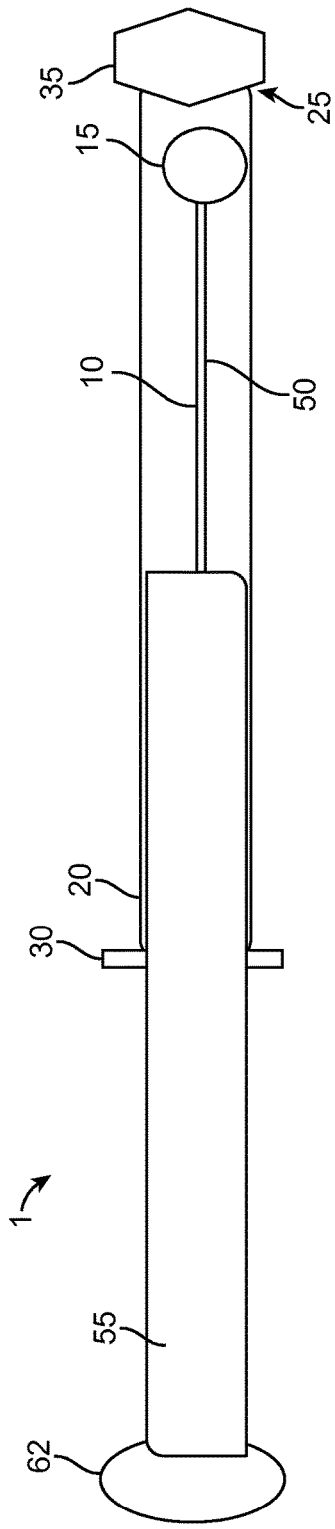
Figure 2C:
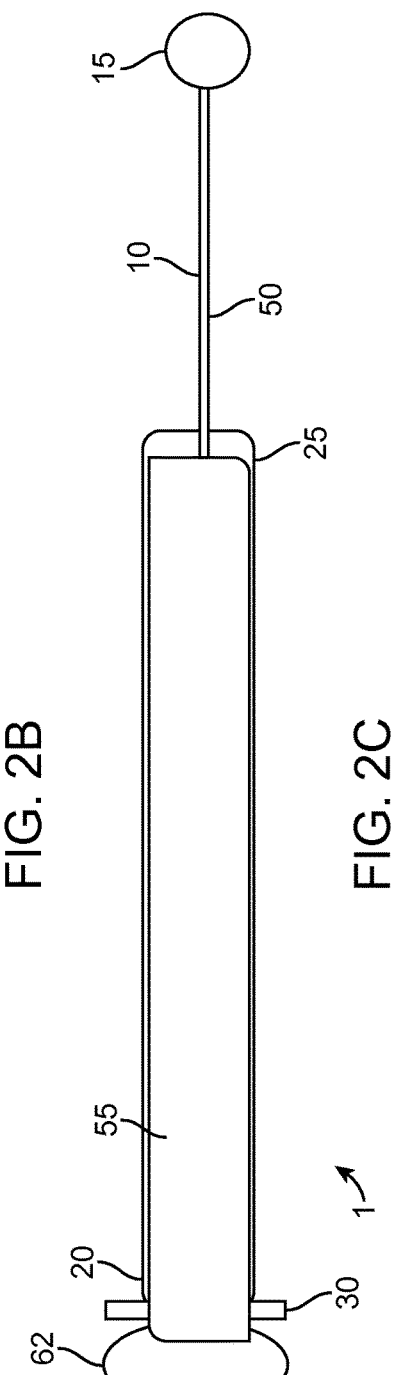
Figure 3:
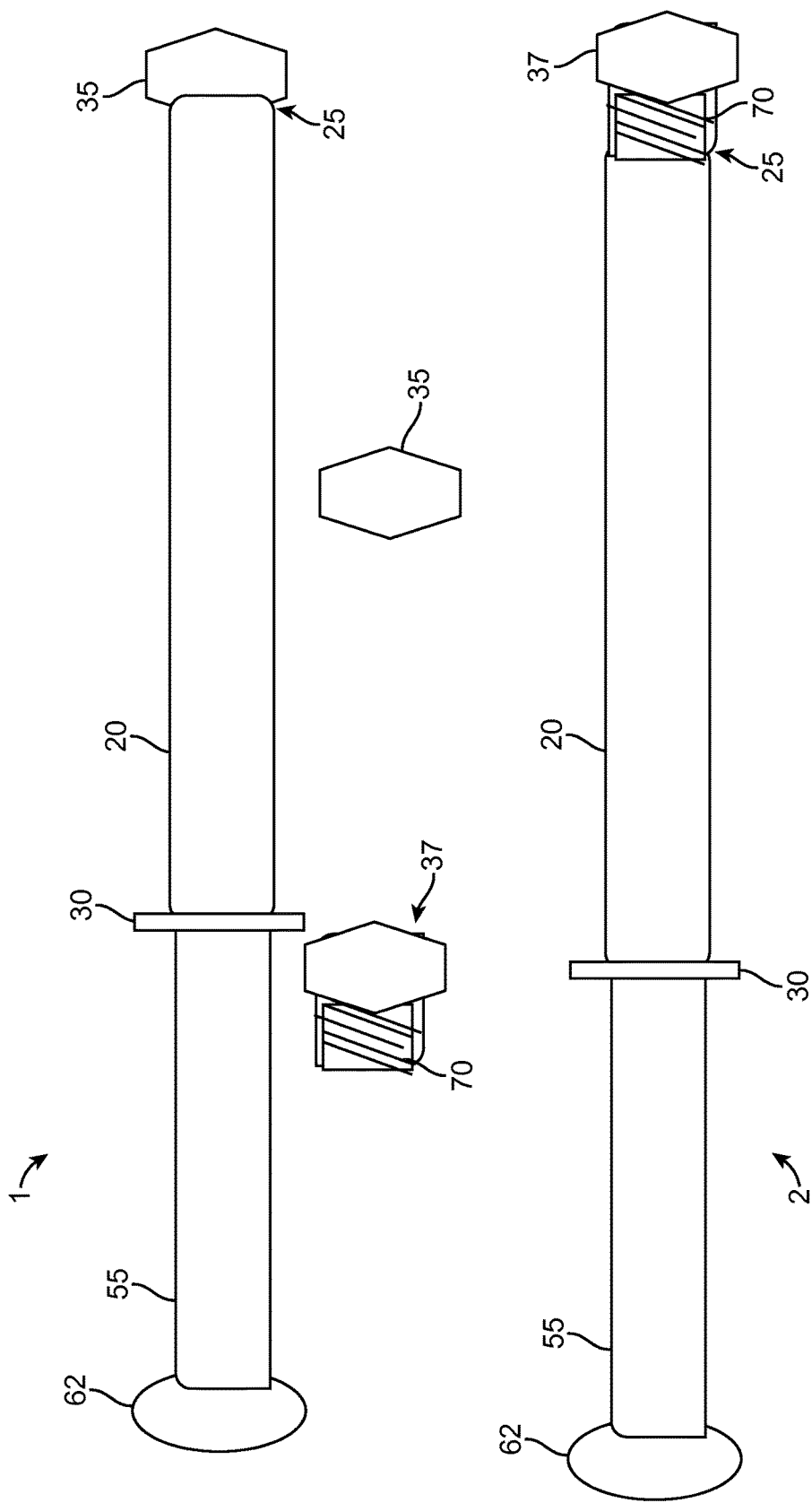
FIG. 3 is a schematic side elevation of an assembled collection device having a plunger or plunger-like device, elongated shaft and collection tip within an outer protective housing that has a removable cap attached thereto, a schematic side elevation of a cap containing a desiccant, a schematic side elevation of a cap without a desiccant, and a schematic side elevation of an assembled collection device having a plunger or plunger-like device, elongated shaft and collection tip within an outer protective housing that has a removable cap containing a desiccant attached thereto.

FIG. 2 shows an assembled collection device, assembled from the components shown in FIG. 1. FIG. 2A is a side elevation of a structure 55 (e.g., plunger) as shown in FIG. 1C and an elongated shaft 10 and collection tip 15 as shown in FIG. 1A. In FIG. 2A, the elongated shaft 10 is positioned or disposed within the elongated opening 60 of structure 55 (e.g., a plunger). In this embodiment, the collection tip 15 is attached to the first end 40 of the elongated shaft 10 such that the collection tip 15, and optionally an adjacent portion of the first end 40 of the elongated shaft 10, is mechanically separable from the elongated shaft 10 or a portion of the elongated shaft 10. The area 50 of the elongated shaft 10 that is separable may sometimes be referred to as a "breakaway point" and in some embodiments, may be snapped, broken or severed to separate the collection tip 15 from the elongated shaft 10 or a portion of the elongated shaft 10. FIG. 2B is a side elevation partially in cross section of an assembled collection device 1 having structure 55 (e.g., a plunger), elongated shaft 10 and collection tip 15 of FIG. 2A within an outer protective housing 20 that has a removable cap 35 attached thereto. In FIG. 2B, the elongated shaft 10 and collection tip 15 are in a first protected position within the outer protective housing 20 which has a removable cap 35 attached thereof. FIG. 2C is a side elevation partially in cross section of the assembled collection device of FIG. 2B in which the collection tip 15 is in a second collecting position outside the outer protective housing 20 and the removable cap 35 has been removed. In the embodiment shown in FIG. 2, the combination of structure 55 with the elongated shaft 10 and collection tip 15 and the outer protective housing 20 (and optionally the removable cap 35) forms a syringe or syringe-like collection device 1. When in use, pressure can be applied to the handle or knob 62 of structure 55 (e.g., plunger) to move the carrier 10 and collection tip 15 between protective and collecting positions.

In some embodiments, the collection device can include a desiccant for drying and preserving the sample being collected. In such an embodiment, the desiccant is typically contained within a removable cap or within a cap that is operably coupled to the outer protective housing. Referring to FIG. 3, this figure shows two embodiments of a collection device 1, 2, both including a removable cap. The top collection device 1 is shown with a removable cap 35 that does not contain desiccant 70. Below the top collection device 1 is shown a removable cap 37 having desiccant 70 within, and a removable cap 35 without desiccant 70. The lower collection device 2 is shown with a removable cap 37 having desiccant 70 within. In an embodiment in which a desiccant is included, any suitable desiccant can be used. Examples of suitable desiccants include silica gel, 8 mesh dri-rite optionally with color indicator, etc.

Soluble and Hydrophilic PCL

PCL is a biodegradable polyester that is insoluble in water and retains its hydrophobic character when mixed with other resins and plastics. PCL has a low melting temperature (60° C.) and is easily malleable making it ideal for certain molding applications. PCL is hydrophobic and water beads form on its surface upon exposure and untreated PCL has low hydrophilicity (i.e., a low affinity for water; not easily absorbing or dissolving in water). In a typical embodiment of a collection device as described herein, the collector tip includes PCL that has been modified or treated to be soluble (e.g., at least partially soluble) and hydrophilic. In such an embodiment, the PCL is at least partially soluble such that at least 50% of the PCL solubilizes when contacted with a biologic analyte extraction reagent, depending upon the biologic analyte extraction reagent and conditions used. Typically, however, greater than 85% of the modified (treated) PCL solubilizes when contacted with a biologic analyte extraction reagent. For example, in an embodiment in which the collection tip includes modified PCL and the sample includes nucleic acid, contacting the collection tip with the sample adhered thereto with a nucleic acid extraction reagent generally results in separation of about 70% to about 90% of the nucleic acid from the collection tip.

Collection tips, typically made of soluble and hydrophilic PCL, efficiently adsorb samples of various types such as bodily fluids, cells shed from fingerprints, and the like, with no or limited adverse affects to targeted samples. Such materials release samples with high efficiency using, for example, commercially available DNA extraction kits. PCL can be modified to be soluble (e.g., at least partially soluble) and hydrophilic as described in U.S. Pat. No. 8,759,075, incorporated herein by reference. PCL as presented herein is modified to improve its hydrophilicity. Such PCL modification enhances absorbency, sterility and freedom from contaminating DNA. PCL can be modified using any suitable chemical or physical methods. One or more surface features of PCL can be modified (or added) to increase hydrophilicity.

PCL is a homopolymer made by a ring-opening polymerization of epsilon caprolactone. Similar polymers are polylactide, polyglycolide or polydioxanone. PCL may be copolymerized with other esters such as polylactide to alter properties. In addition to polylactide, PCL may be copolymerized with other lactone-containing polymers such as poly-glycolide, poly (3 to 10-membered) lactone ring-containing compounds, etc. Generally, high molecular weight (MW) biodegradable lactone co-polymers are used, but poly ethylene glycol and poly vinyl styrene can also be used. In a typical embodiment, a molecular weight range of PCL is 5K to 300K. For example, an 80K MW PCL polymer can be used.

Polymers of acrylamide may also be used, such as poly N-isopropylacrylamide. The addition of derivative groups to the PCL polymerization reaction may be used to change properties of the PCL. For example, the carbohydrate trehalose can be used to enhance DNA stability. Soluble, hydrophilic PCL can be impregnated with a bacteriostatic or fungicidal substance to inhibit bacterial growth for samples in storage. Other possible modifications include inhibitors of enzymes (such as DNAse or other nucleolytic enzymes) that can degrade the sample. In other approaches, soluble, hydrophilic PCL can be modified by coupling a protein to PCL, such as an antibody.

An important factor in obtaining a high yield of DNA, for example, from biological samples is the ability of the collection material to release the material and the extracted DNA into extraction reagent solutions. The fact that the collection tips described herein (e.g., hydrophilic, at least partially soluble PCL) dissolve (are solubilized) in most of the commonly used extraction solutions facilitates high yields of DNA. Success of DNA typing is related to the amount of target material recovered from an evidentiary item. Generally, the more DNA that is recovered, the better the chance is of obtaining a typing result that will be robust and reliable. A favored method of collecting stain materials is by swabbing. The collection devices described herein can be used by swabbing. Successful recovery of DNA relies on two qualities of a swab, i.e., absorption and adsorption. The two features impact the ability to collect materials from a stain or surface and then release the cells/DNA during the extraction process. Swabs that are proficient at collecting materials often are less efficient at releasing DNA from the swab matrix, and vice versa. Indeed, it is well-known that recovery of DNA from a conventional swab is inefficient. In fact, van Oorschot et al. (van Oorschot R A, Ballantyne K N, Mitchell R J. Forensic trace DNA: A review. Investig Genet. 2010 12; 1(1):14, 2223-1-14) suggested that a significant proportion of DNA (20-76%) that is collected by a cotton cloth/swab is lost during the extraction phase which may be attributed to the collecting agent (swab, cloth, etc.) and the condition of the sample.

Recovery of DNA from a number of commercially-available swabs reveals that this is not an efficient process. By contrast, a collection tip made of PCL modified and prepared according to the methods of U.S. Pat. No. 8,759,075, (e.g., Diomat™ from Diomics Corp., San Diego, Calif.) is a unique bio-specimen collection material with highly absorptive properties and can be disrupted and at least partially dissolved during certain extraction conditions. Therefore, more DNA may be collected from a substrate and be released from the collection tip than currently known swabs.

Methods of Producing Collection Devices

A collection device as described herein can be produced by any suitable method. Collection devices can be produced individually, or produced several (e.g., a plurality) at a time (e.g., in bulk, large-scale production, etc.). In a general method, a collection tip is attached to a carrier by introducing or inserting the carrier into a container (e.g., block, tray, well, mold) containing liquid PCL. For example, for producing a plurality of collection devices, a multi-well plate, tray or platform may be used, in which each well contains liquid PCL, and into each well is inserted a carrier. In this example, multiple carriers can be suspended from a block or other substrate placed above the multi-well plate, tray or platform such that each carrier is aligned with an individual well, allowing lowering of the block or other substrate such that each individual carrier is lowered into its own individual well containing PCL. Once the carriers are lowered into the wells of PCL, the entire arrangement (i.e., multi-well plate, tray or platform and block or other substrate with suspended carriers) is subjected to a sufficiently cold temperature for freezing the PCL resulting in attachment of the PCL to the carrier(s). The resultant plurality of collection tips operably coupled to carriers is separated from the multi-well plate, tray or platform and from the block or other substrate, and the PCL can be treated with a base to render the PCL hydrophilic as described above. The hydrophilic PCL is then typically neutralized and dried, and subsequently, the plurality of collection tips operably coupled to carriers can be subjected to quality control processes. Each collection tip operably coupled to a carrier is combined with an outer protective housing, and optionally a cap, by any suitable method, resulting in a collection device as described herein. Each collection device can be packaged individually and sterilized. The collection device can be sterilized prior to packaging, after packaging, or both. Before or during packaging, the collection device can be labeled in some way. Additionally or alternatively, after the collection device is packaged, the packaging can be labeled in some way. Specific examples of methods for producing collection devices are included in Examples 1-3 below and in FIG. 4.

Figure 4:
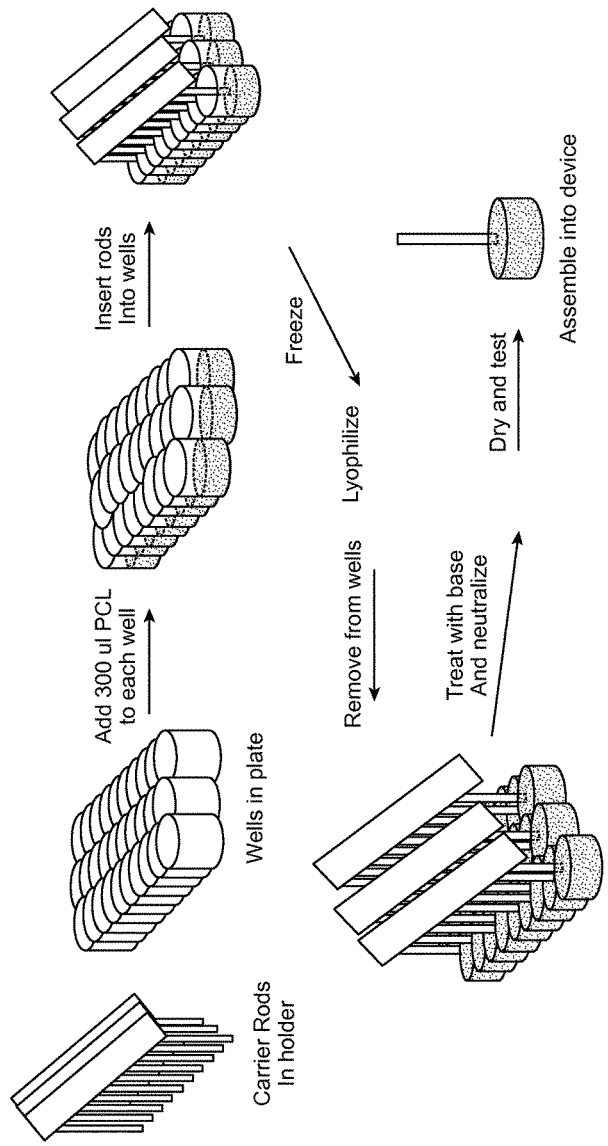
FIG. 4 is a schematic illustration of one embodiment of a process for producing a collection device as described herein.

In FIG. 4, one example of a method of producing collection devices involving implementation of a holder device is shown. In this method, the holder device is loaded with carrier rods at a depth and orientation such that, upon placement atop the well plate, each rod is centered in its well at an appropriate height. The now-loaded holder is sterilized and dried, and the well plate is loaded with 300 microliters of PCL solution in each well. The loaded holder is then lowered onto the well plate with each rod in a well. The holder/plate assembly is then placed in a lyophilizer and undergoes first freezing, then lyophilization, according to protocol. Upon the completion of the lyophilization protocol, the holder with rods is separated from the well plate so that the tip of each rod is capped with a tip of PCL which will be processed to become Diomat™. While still mounted in the holder, the PCL-coated tips are treated with (aqueous) base (for a specified amount of time) before being neutralized and then dried. At this point, the Diomat™-tipped rods are removed from the holder and can, after appropriate testing, be attached to, for example, a syringe device.

Samples and Biologic Analytes to be Collected and Analyzed

Samples include any biologic analyte (e.g., nucleic acid)—containing material (e.g., a biologic material). Samples may be those obtained directly from a subject (e.g., a human subject) or those indirectly obtained from a subject (e.g., samples that have been processed in some way prior to obtainment from the subject, samples left at a crime scene, etc.). Types of useful samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, autopsy samples, infection samples, nosocomial infection samples, production samples, drug preparation samples, biological molecule production samples, protein preparation samples, lipid preparation samples, carbohydrate preparation samples, fingerprints, cells shed from fingerprints, etc. Types of forensics samples include blood, dried blood, bloodstains, buccal swabs, touch samples (e.g., epithelial cells left on the lip of a drinking glass, the inner rim of a baseball cap, or cigarette butts), nucleated cells obtained by various means and material taken in forensic investigations that may include cells shed in fingerprints, laser-dissected cells, chewing gum, gastric contents, saliva, nail scrapings, soil, sexual assault samples including sperm and vaginal epithelial cells, hair, bone, skin, any bodily fluid, and solid tissue.

A typical biologic analyte is a nucleic acid. Nucleic acids include, for example, mammalian (e.g., human) nucleic acids, bacterial nucleic acids, or viral nucleic acids. A nucleic acid (or nucleic acid sample) can be, for example, from one or more cells, tissues, or bodily fluids such as blood, urine, semen, lymphatic fluid, cerebrospinal fluid, or amniotic fluid, or other biological samples, such as buccal swabs, mouthwashes, stool, tissue culture cells, tissues slices, biopsy aspiration, etc. Nucleic acids can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwashes, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, etc. A sample or nucleic acid sample may also contain mixtures of material from one source or different sources. For example, nucleic acids of an infecting bacterium or virus can be present along with human nucleic acids when nucleic acids from such infected cells or tissues are collected and analyzing using the disclosed methods.

Methods of Collecting and Optionally, Analyzing, a Biologic Analyte

A method of collecting and optionally analyzing at least one sample (e.g., a forensics sample, a medical diagnostic sample) containing a biologic analyte includes contacting the at least one sample (e.g., cells, tissue, blood, urine, semen, lymphatic fluid, cerebrospinal fluid, amniotic fluid, buccal swab, mouthwash, stool, tissue culture cells, tissues slices, tumor biopsy, biopsy aspirate, etc.) with a collection device as described such that at least a portion of the at least one sample is reversibly adhered to the collection tip (e.g., a collection tip made of hydrophilic and at least partially soluble PCL). In an embodiment in which the sample is analyzed after collection, the method includes contacting the collection tip and the reversibly adhered sample with at least one biologic analyte extraction reagent under conditions such that the collection tip is at least partially solubilized and the sample is separated. In one embodiment, the collection tip can be separated from the carrier, and the collection with sample reversibly adhered thereto can be contacted with (e.g., immersed in) the biologic analyte extraction reagent (see the collection device of FIG. 2A). A method of collecting and optionally analyzing at least one sample can further include collecting the separated sample, and separating the biologic analyte from the sample. In one embodiment, the biologic analyte is nucleic acid (e.g., eukaryotic or prokaryotic genomic DNA, oligonucleotide, mitochondrial DNA, cDNA, STR, bacterial plasmid, and bacteriophage DNA) and separating the biologic analyte from the sample includes subjecting the separated sample that includes the biologic analyte to a nucleic acid extraction reagent and extracting the nucleic acid from the separated sample. In such an embodiment, the process can result in separation of about 70% to about 95% of the nucleic acid from the collection tip.

The method can further include the step of analyzing the biologic analyte. For example, the sample can be obtained from a human subject, the biologic analyte can be at least one nucleic acid, and analyzing the biologic analyte can include nucleic acid sequencing. In this example, analyzing the biologic analyte (the nucleic acid) can result in a DNA profile and determination of the human subject's identity. Analyzing the biologic analyte can further include comparing the DNA profile to a reference sample. Analyzing the biologic analyte can include any appropriate methodology, including, for example, nucleic acid sequencing, forensic analysis, Combined DNA Index System (CODIS), protein assay, chemical analysis, immunoassay, mass spectrometry, microarray analysis, and detection of radioactive material. In the collection devices, methods, and kits described herein, sufficient nucleic acid (e.g., DNA) is typically extracted from a sample such that amplification of the extracted nucleic acid is not required prior to specific analysis. However, in an embodiment in which amplification is useful or required, any suitable method for amplifying a nucleic acid may be used. Methods of polymerase chain reaction (PCR) amplification are well known in the art.

In a method that further includes the step of analyzing the biologic analyte, as mentioned above, the sample may be from a patient and analyzed for diagnosing disease in the patient, monitoring disease progression in the patient, analyzing drug or other treatment efficacy in the patient, etc. These methods may be used to obtain biologic samples for diagnostics (medical diagnostics), where biologic samples (e.g., blood, urine saliva, mucus or other body component or fluid) may be collected from individuals (e.g., patients) for the purpose of detecting disease, measuring its severity, and/or monitoring effects of treatment (treatment efficacy, drug efficacy). In a diagnostic embodiment, the sample(s) obtained and analyte(s) measured may depend on the specific disease or condition to be detected or monitored. In such embodiments, individuals tested may have undetected disease or may be tested to monitor progress of disease or response to treatment.

Generally in these methods, prior to use of a collection device, the collection tip of the device is shielded from exposure to contamination by containment in the outer protective housing (e.g., a sheath of plastic, metal, rubber or glass). In a typical embodiment, the collection tip is retractable, and various mechanisms of retractable action may be employed. For example, the collection tip may be extended for use (collection) by the user pushing on a lever-like projection (similar to a utility knife). In another example, the collection tip may be held by a spring that is released and the collection tip may extend directly in a straight line or may open like a folding knife. As shown in FIGS. 1-3, the collection device may be a syringe-like device involving a plunger (e.g., consisting of a handle with a rubber suction cup at one end). In a typical method, after sample collection, the collection tip is retracted into the outer protective housing and the sample is dried in the presence of a drying agent (desiccant) contained within the collection device, typically within the cap. In this way, the sample is maintained dry and free from exposure to atmospheric contaminants until extraction of the biological analyte (e.g., nucleic acid) is accomplished by immersing the collection tip into a biologic analyte extraction reagent (e.g., a nucleic acid extraction reagent).

Methods of Genotyping a Sample

In one embodiment, a collection device as described herein can be used for genotyping a sample that includes a nucleic acid. In this embodiment, the method typically includes the following steps: collecting or providing the sample using a collection device as described herein, wherein the sample is reversibly adhered to the collection tip of the collection device; contacting the collection tip and the sample with at least one nucleic acid extraction reagent under conditions such that the PCL is solubilized and the sample is separated from the collection tip; separating the nucleic acid from the sample; and analyzing the nucleic acid for a plurality of genetic markers at a plurality of STR loci and generating a DNA profile. The sample can be, for example, a human buccal sample or blood sample. Alternatively, the sample can be obtained from a fingerprint (e.g., cells present in or shed from a fingerprint).

The method can further include assigning a Specimen Identification Number to the DNA profile, and/or comparing the DNA profile to at least one other DNA profile in at least one DNA database. Exemplary embodiments of this method are described below.

The collection devices described herein are made from materials that do not react with a collected sample or specimen in unexpected ways, unless configured to do so, and preferably are not effected by exposure to altered levels of various environmental conditions, such as elevated ultraviolet (UV) light. The collection devices, methods and kits described herein provide nucleic acids and nucleic acid samples that when analyzed, provide data suitable for forensic interpretation. Forensic interpretation guidelines are known, and are described, for example, in Scientific Working Group on DNA Analysis Methods, Short Tandem Repeat (STR) Interpretation Guidelines. Forensic Science Communications, 2000, 2(3). In a typical embodiment, sample/specimen profile analysis data is reportable in a format usable with the Combined DNA Index System (CODIS), for example. CODIS provides a searchable database of DNA profiles to assist in the identification of suspects in crimes.

A commonly used method for identification of DNA samples for forensic purposes relies upon typing of STRs (short tandem repeats) at 13 polymorphic autosomal loci coupled with analysis of the amelogenin gene to determine gender of the sample donor, i.e., the system of CODIS. CODIS is a software platform that blends forensic science and computer technology. CODIS has multiple levels where DNA profiles can be stored and searched: the local level (for city and county DNA laboratories), state level and national level. Data stored at the national level is kept in the National DNA Index System, or NDIS. At this level, an analyst can try to match a DNA profile from a local crime scene sample (also known as a forensic unknown) with an offender's profile from across the nation to solve cases that span states. Analysts use CODIS to search DNA profiles obtained from crime scene evidence against DNA profiles from other crime scenes and from convicted offenders and arrestees. CODIS can generate investigative leads in cases when a match is obtained. For example, if the DNA profile from a crime scene matches a sample taken from another crime scene, the cases may be linked in what is called a forensic hit. If the crime scene sample matches a convicted offender or arrestee sample, the result is called an offender hit. Hits give investigating officers valuable information that helps them focus their investigation. CODIS identifies autosomal genetic markers at 13 STR loci, plus Amelogenin (AMEL) to determine sex. The term "CODIS STR loci" as used herein refers to the thirteen core STR loci designated by the FBI's "Combined DNA Index System." The thirteen core STR loci are TH01, TPDX, CSF1PO, vWA, FGA, D3S1358, D5S818, D7S820, D13S317, D18S539, D8S1179, D18S51, and D21S11. (See, e.g. Vallone et al. For SCi Intl Genetics 3, page 42, 2008; and Butler, Forensic DNA Typing, Academic Press (2001), at page 63.) Use of the CODIS is well known in the art. The 13 loci listed above that are used in the CODIS have been well characterized. See, for example, U.S. Pat. No. 8,562,918. This patent is incorporated by reference herein in its entirety.

Accordingly, in a method of genotyping a sample that includes a nucleic acid as described herein, the method can include comparing the DNA profile obtained to at least one other DNA profile in at least one DNA database using CODIS software. In this embodiment, the at least one DNA database is typically the National DNA Index System, and optionally, a state DNA database. The plurality of genetic markers are typically alleles, and the plurality of STR loci can include one or more CODIS STR loci (i.e., D3S1358, TH01, D21S11, D18S51, D5S818, D13S317, D7S820, D16S539, CSF1PO, vWA, D8S1179, TPDX and FGA). Some embodiments of genotyping a sample include generating a profile of the DNA in the sample, comparing the generated profile with profiles of DNA stored in a database, and upon determining that the generated profile matches one of the stored profiles, identifying the source from which the stored profile was obtained. In forensics, a DNA profile may include a DNA "fingerprint" of multiple, polymorphic genomic loci within a given nucleic acid template, which can then be used in some embodiments to identify the individual (or information about the individual or blood relatives of the individual) from which the nucleic acid template was obtained.

The typical process for typing the CODIS markers is to first isolate DNA from the biologic sample collected and then amplify this sample with primers specific for human DNA in order to provide sufficient material and to avoid amplification of microbial or other possible contaminating non-human DNA. However, using the collection devices, kits and methods described herein, sufficient human DNA is present in and obtained from the primary sample such that this preliminary amplification step is unnecessary except in the case of very low-copy samples such as fingerprints or trace samples.

The sample is then amplified by PCR (polymerase chain reaction) using 15 different primer sets to give samples of each relevant locus. The amplicons for a given locus will have a size reflective of the number of repeats encoded in the sample donor. These will then by separated by capillary electrophoresis and the profiles compared to known genotypes. As with all polymorphic human genes, a given individual's sample may have one or two of the possible alleles depending on whether they are homo or heterozygous at that locus.

The PCR amplification of the 15 loci may take place in separate tubes, there may be groups of genes typed in several tubes or, most efficiently, all will be amplified in the same tube. These splitting or lumping schemes depend on the ability to analyze the various mixes of amplified products. Different strategies to give separation for the various loci have been developed. Two common methods to differentiate one locus from another are 1) use different lengths of the flanking sequences to give size separation and 2) use different dye markers coupled to the PCR primers to give different signals from overlapping peaks when the final products are detected. Subsequently, capillary electrophoresis is used, yielding a tabulated result for typing of a known subject. The frequency at which a subject's genotype is found in a particular population (e.g., a Caucasian population) can be determined using known methods. This methodology is described, for example, in Vallone et al. For SCi Intl Genetics 3, page 42, 2008.

In one embodiment of a method of genotyping a sample as described herein, the entire group of CODIS loci is amplified in a single tube and the profile resulting from this is analyzed in a single run on the capillary electrophoresis instrument. Refinements of this process might include elimination of the first amplification step and automated handling of samples throughout the DNA extraction, amplifications and sample loading and software to determine the genotype and convert it to a form that may be stored in the reference bank. The collection devices described herein are designed to capture sufficient sample and to yield a high percentage of the DNA contained within it thus allowing the standard CODIS analysis to be performed directly upon extraction of the DNA.

In addition to the STR analysis in current use, DNA samples may be subject to more complete determinations such as full-length genomic sequences, specific gene sequences, methylation status of DNA sequences, mtDNA analyses. For example, the increasing use of high throughput DNA sequence analyzers can influence the way in which samples are analyzed in the future and will make the quality of the DNA obtained more highly relevant to the information that can be obtained.

Data obtained about the DNA of a subject using the collection devices, methods and kits described herein may be stored for subsequent retrieval, such as in a DNA database (e.g., the CODIS). Subsequent cross-comparison of DNA profiles may be made with such information. DNA information may be employed for solving unsolved or "cold" cases (e.g., unsolved cases), for solving property crimes, for identifying persons or victims, or for some other purpose. One or more collection devices as described herein may be provided as part of a forensic analysis kit. Any of the kits herein may include one or more additional components adapted for nucleic acid collection and typing. Such a kit may include, for example, one or more extraction reagents, buffers for storage and reactions of the DNA, PCR primers, etc.

Stability of collected samples (e.g., biological samples) is critical for accurate analysis and profiling. Results obtained from analyses of the collected samples should be comparable irrespective of the time interval between collection and analysis. In some embodiments, analyses are not performed immediately after sample harvest and there are a number of chemical and biological agents and conditions that can affect the integrity of the sample or of the nucleic acid (e.g., DNA) from it. Insulation from atmospheric conditions by storage in temperature and humidity controlled areas is common to preserve sample integrity. Several methods are known to preserve purified DNA from degradation after primary processing of the samples at the analytical laboratories. The carbohydrate trehalose is one of the compounds currently used as a stabilizer for dried DNA during storage. It is most effective when the purified DNA is stored at about of range of −60° C. to −90° C., and preferably about −80° C. or at ambient temperature (e.g., about 18° C. to 25° C.). In one embodiment, trehalose can be mixed with PCL to increase the hydrophilicity of the PCL and, at the same time, give greater stability to the DNA in the sample from the moment of collection. As described above, in some embodiments, the collection device includes a cap that contains a desiccant for drying and preserving the sample.

Kits for Collecting and Optionally, Analyzing, a Sample

Kits for collecting, and in some embodiments also analyzing, a sample will find particular use in forensic analyses and medical applications (e.g., diagnostics). A kit for collecting at least one sample (e.g., sample including a nucleic acid) includes at least one collection device as described herein, a biologic analyte extraction reagent (e.g., a nucleic acid extraction reagent), instructions for use and packaging. The packaging can be any suitable material, e.g., a polymer laminate or plastic container. In one embodiment of a kit, the kit includes a plurality of collection devices as described herein. Generally, in such a kit, each collection device is disposable, and intended for one use only. In such a kit, each collection device can be individually packaged, and each packaged collection device can include an identifying label, bar code, and/or RFID tag. In such an embodiment, the identifying label, bar code, and/or RFID tag is typically affixed or connected to the packaging. However, in some embodiments, the identifying label, bar code, and/or RFID tag is affixed or connected to the collection device. In some embodiments, each collection device of a kit is packaged with a desiccant. The desiccant can be within the cap, or can be contained or disposed within the packaging.

In many applications, the collected sample is not analyzed immediately upon acquisition (collection). An identification means to assure that the collector (collection device or collection tip) and the sample can be processed without danger of losing the sample information can be attached to or included with a sample collection device, kit or apparatus as described herein, e.g., affixed or otherwise attached to a collection device or to a package in which one or more collection devices are packaged. The use of bar codes or quick response ("QR") codes (or other identifying indicia) placed on the packaging at the time of manufacture is one example of a means of retention of sample identity, and in such embodiments, the data linking the collector information with the sample is typically secure. A collection device or kit as described herein can include one or more of: an RFID tag, a bar code, and a label (e.g., two or more of an RFID tag, a bar code, and a label; all of an RFID tag, a bar code, and a label). An RFID tag can be imprinted with information, such as a bar or QR code. This manufacturer-supplied information can include lot and serial number to unambiguously identify the collection device. Sample collection devices, such as in forensic applications, are used to obtain samples of biological materials for subsequent analyses that serve to establish the identity of the sample source by subsequent analytic steps. How a programmable RFID tag can be implemented in forensic specimen collection, for example, is well known in the art. See, for example, U.S. Pat. Nos. 7,978,074 and 8,759,075, both of which are incorporated herein by reference. The sample collection device may be subject to analyses immediately or it may be stored for some period of time prior to analysis. Often multiple samples must be taken (for example at a crime scene). In this instance the samples may not be analyzed for long periods of time because of a backlog in the laboratory, or the need to send samples for tests not available near the scene of collection. Therefore, in such embodiments, it may be particularly helpful if certain identification criteria accompany the sample.

The present kit embodiments can provide a reagent set that yields information on the quantity of DNA obtained at the collection site. This allows collection of additional samples should the amount be found inadequate. In one embodiment, a kit is provided that allows initial steps of the analytic process to begin in the field and to give an indication of the quantity of DNA obtained. Such a kit can include one or more collection devices as described herein packaged with DNA extraction reagents in lyophilized form. In this embodiment, a rapid amplification of DNA follows subsequent to extraction. Following the amplification of the extracted DNA, a colorimetric indicator can be used as a signal that there is (or is not) adequate DNA for complete analysis. This colorimetric indicator can be a DNA-indicating dye included in the reagent, or alternatively, on an impregnated paper to which a drop of solution is added.

In one approach, a kit is provided for use in forensic analyses that can perform the initial steps subsequent to sample collection (such as sample preparation and/or analysis) and also to signal a user that sufficient DNA has been obtained to allow complete analysis of the sample. In other embodiments, a kit can be used in medical analyses for collecting and analyzing a biological sample(s) from a patient(s), and can perform the initial steps subsequent to sample collection (such as sample preparation and/or analysis) and also to signal a user that sufficient biological analyte (e.g., DNA, protein, etc.), has been obtained to allow complete analysis of the sample.

Those skilled in the relevant art will appreciate that the embodiments described herein can be practiced with any of various communications, data processing, or computer system devices, including: hand-held devices (including personal digital assistants (PDAs)), wearable computers, cellular or mobile phones, multi-processor systems, microprocessor-based or programmable consumer electronics, network PCs, mini-computers, mainframe computers, and the like. Aspects of the invention described herein may be stored or distributed on computer-readable media, including magnetically or optically readable computer discs, hard-wired or preprogrammed chips (e.g., EEPROM semiconductor chips), nanotechnology memory, biological memory, or other data storage media. Computer-implemented instructions, data structures, screen displays, and other data under aspects of the invention described herein may be distributed over the Internet or over other networks (including wireless networks), on a propagated signal on a propagation medium (e.g., an electromagnetic wave(s), a sound wave, etc.) over a period of time, or they may be provided on any analog or digital network (packet switched, circuit switched, or other scheme).

Nucleic Acid Extraction Methodology

Several of the methods described herein involve extraction of a nucleic acid from a sample. These methods can be used in forensics as well as medical applications. Nucleic acid extraction can be performed using any suitable methodology. With regard to forensics, for example, samples taken from crime scenes and those used as references to identify these acquired samples must go through a several step process to yield data suited for comparison and identification. The first step is sample collection that may involve swabbing stains from a crime scene or taking a blood or buccal cell sample from a suspect for comparison. (If no suspect has been identified, the data obtained may be compared to samples in databases maintained by the FBI and other law enforcement agencies.) The sample is then stored in a manner to prevent any contamination by cells from other individuals and is kept dry to avoid growth of any biologic agents, such as bacteria or fungi, that may degrade the sample. The next step is extraction of DNA and quantification to determine if there is sufficient for the subsequent analyses.

Extraction and purification of nucleic acids, proteins or other biologic analytes from samples using conventional techniques are significant challenges. Since molecular genetics, genomics and informatics will be central to future diagnostics, the methods described herein involving DNA collection (recovery) are suited for subsequent analyses by standard genetic typing used for forensics samples. However, the rapid progress in obtaining whole genome sequences by newly developed techniques and instrumentation makes it mandatory to retrieve sufficient quantities and to maintain the integrity of nucleic acids for sequencing. Any techniques used must optimize the chances of characterizing the material to the highest possible level without costly retesting.

Extraction is usually necessary as a sample-processing step between collection and analysis. A wide variety of options exist for extracting nucleic acids for analysis. Ideally, extraction protocols should be simple and inexpensive to perform. A collection medium should be compatible with a number of extraction procedures. Standard DNA extraction procedures may entail 1) organic solvent, 2) salting out methods, 3) cation exchange resins, such as Chelex-100; or 4) silica-based methods (2,6-11) Many laboratories are moving away from organic phenol-chloroform extraction because of the toxic reagents involved, although it still is one of the best extraction procedures for purifying nucleic acids. Examples of preferred non-organic methods include silica-based methods, such as QIAquick® columns (Qiagen, Valencia, Calif.), which utilize silica membrane spin columns to bind and elute DNA. The bind-capture-elute methods have proven to be successful for purifying DNA for the PCR from samples containing inhibitors.

Methods involving conventional molecular biology techniques are described herein. Such techniques are generally known in the art and are described in detail in methodology treatises such as Molecular Cloning: A Laboratory Manual, 3rd ed., vol. 1-3, ed. Sambrook et al., Cold Spring Harbor Laboratory Press, Cold Spring Harbor, N.Y., 2001; and Current Protocols in Molecular Biology, ed. Ausubel et al., Greene Publishing and Wiley-Interscience, New York, 1992 (with periodic updates).

EXAMPLES

The present invention is further illustrated by the following specific examples. The examples are provided for illustration only and should not be construed as limiting the scope of the invention in any way.

Example 1—One Embodiment of a Manufacturing (Production) Process

In one embodiment, a collection device is made by the following method. The collection tip is attached to a stick-like carrier which is connected to the retraction mechanism. The collection tip on the stick is manufactured separately and subjected to rigorous testing before being attached to the completed device. This process utilizes plastic blocks or trays into which liquid PCL is introduced, a carrier stick is added—sticks may be suspended from a block with spacing of holes equal to the wells containing PCL. This block with carriers is placed in a parallel position to the wells of PCL and the PCL is then frozen. After freeze drying, the sticks with PCL attached at one end (the end inserted into the wells containing PCL) are removed from the blocks or trays and treated to render the PCL hydrophilic by treatment with a base as described above. After neutralization and drying, the sticks with PCL collection tips are subjected to quality control and upon passing suitable control quality requirements, the batch is then attached to a retraction device which may be mass-manufactured by injection molding according to specific plans. After assembly and capping the device is packaged, the units are labeled and sterilized and are ready for use.

Example 2—An Embodiment of a Manufacturing (Production) Process

In one embodiment, the collector portion (collection tip) of the device is made from PCL, which is dissolved in glacial acetic acid in a defined weight percentage such as 2% to 8% with a preferable 6% by heating for 1 to 4 hours with a preferred two hours and cooling to room temperature for 30 minutes to 4 hours with a preferred one hour. This solution is of acceptable quality for up to 3 days from production. This room temperature, clear colorless solution is added to an appropriate mold, such as a 96-well plate, dish, glass, metal, parchment paper, Teflon, plastic, foam, paper, or other apparatus. An appropriate amount of polymeric solution is added to the mold, the materials are cooled to −20° C. for 1 to 48 hours with a preferred cooing of 2 to 3 hours, followed by cooling to −40° C. to −103° C. for 1 to 48 hours with a preferred cooling of −40° C. for 2 to 3 hours followed by sublimation of the acetic acid through a freeze-dry or lyophilization process by decreasing the pressure through a vacuum pump apparatus protected by a condenser at a −48° C. to −113° C. temperature preferably at a −81° C. temperature and a base trap, preferably a soda sorb base trap using a Mass Vac Posi-Trap apparatus. The pressure is dropped from room atmosphere of 760 torr through a series of steps down to 100 mtorr and kept there until the acetic acid has been thoroughly sublimed through lyophilization. On completion of lyophilization process, vacuum is released, and product is collected. A base treatment with 1M to 2M NaOH base for 1 hr to 1 week at 21° C. or at 37° C. and preferably 1.5M NaOH for 2 hrs at 37° C. and 4 hrs at 21° C. is used. Product is neutralized by repeated water washes and thoroughly dried in laminar flow hood for 24-48 hours followed by insertion in snapware container with Dri-rite for 48-96 hours prior to testing. In one means of testing, product is used to acquire biologic samples (such as 1 ul of human blood) and to release DNA from them. If the majority (50% or greater) of DNA in sample, as measured by amount of DNA in the total sample, is released upon extraction, the collection device is deemed acceptable for use and distribution. These collectors on a holder can then be inserted into a retractable syringe-like device for final assembly.

Example 3—An Embodiment of a Manufacturing (Production) Process

One method of producing the retractable holder device is as follows. Concept is made into a 3D CAD model (by "concept" is meant any idea about a possible device or product). From the 3D CAD Model, software is utilized to make a prototype model using 3D printing and ABS plastic. This plastic is thoroughly rinsed with IPA and sanded in rough parts. If the ABS plastic model is of sufficient quality, a mold is formed to make more models using injection molding with a higher quality plastic such as poly propylene (nearly clear and nearly colorless) or poly styrene (White). If a device of sufficient quality is produced, a steel mold is made such that hundreds of thousands of products can be formed using this prototype.

Other Embodiments

Any improvement may be made in part or all of the devices, kits and method steps. All references, including publications, patent applications, and patents, cited herein are hereby incorporated by reference. The use of any and all examples, or exemplary language (e.g., "such as") provided herein, is intended to illuminate the invention and does not pose a limitation on the scope of the invention unless otherwise claimed. Any statement herein as to the nature or benefits of the invention or of the preferred embodiments is not intended to be limiting, and the appended claims should not be deemed to be limited by such statements. More generally, no language in the specification should be construed as indicating any non-claimed element as being essential to the practice of the invention. This invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contraindicated by context.

What is claimed is:

1. A device for collecting a sample, the device comprising an outer protective housing and a collection tip operably coupled to a carrier, the collection tip comprising hydrophilic and soluble polycaprolactone (PCL) that has been treated with a base having a pH greater than 8 and a neutralizing agent for increasing hydrophilicity, the collection tip being movable from a first protected position within the outer protective housing to a second collecting position outside the outer protective housing.

2. The device of claim 1, wherein the outer protective housing comprises a first end a second end, and the device further comprises a removable cap attached to the first end of the outer protective housing when the collector tip is in the first protected position, or a cap that is operably coupled to the outer protective housing.

3. The device of claim 2, wherein the removable cap or the cap that is operably coupled to the outer protective housing comprises a desiccant.

4. The device of claim 1, wherein the hydrophilic and soluble PCL is copolymerized with an acrylamide or a polyester other than PCL.

5. The device of claim 1, further comprising an identifying label or a radio-frequency identification (RFID) tag, or a combination thereof.

6. The device of claim 1, wherein the sample comprises nucleic acid and at least a portion of the collection tip solubilizes when exposed to a nucleic acid extraction reagent.

7. The device of claim 1, wherein the carrier comprises an elongated shaft having a first end and a second end, and the collection tip is attached to the first end such that the collection tip is mechanically separable from the carrier.

8. The device of claim 7, wherein the collection tip and an adjacent portion of the first end of the elongated shaft are mechanically separable from the carrier.

9. The device of claim 1, wherein the carrier comprises an elongated shaft.

10. The device of claim 9, wherein the carrier comprises a plunger having an internal elongated opening for receiving the elongated shaft.

11. The device of claim 10, wherein the outer protective housing and the carrier comprise a syringe, and the collector tip is movable from a first protected position within the outer protective housing to a second collecting position outside the outer protective housing when pressure is applied to the plunger.

12. The device of claim 11, wherein the outer protective housing comprises a first end a second end, and the device further comprises a removable cap attached to the first end of the outer protective housing when the collector tip is in the first protected position, or a cap that is operably coupled to the outer protective housing.

13. The device of claim 12, wherein the removable cap or the cap that is operably coupled to the outer protective housing comprises a desiccant.

14. A kit for collecting at least one sample, the kit comprising:
   i. a plurality of devices for collecting at least one sample comprising nucleic acid, each of the devices comprising an outer protective housing and a collection tip operably coupled to a carrier, the collection tip comprising hydrophilic and soluble PCL that has been treated with a base having a pH greater than 8 and a neutralizing agent for increasing hydrophilicity, the collection tip being movable from a first protected position within the outer protective housing to a second collecting position outside the outer protective housing;
   ii. a nucleic acid extraction reagent;
   iii. instructions for use; and
   iv. packaging.

15. The kit of claim 14, wherein each of the devices comprises an identifying label or a radio-frequency identification (RFID) tag, or a combination thereof.

16. The kit of claim 14, wherein the packaging comprises a desiccant.

17. The kit of claim 14, wherein each of the devices is individually packaged and each package comprises a desiccant.

18. A method of collecting at least one sample comprising contacting the at least one sample with a device for collecting a sample, the device comprising an outer protective housing and a collection tip operably coupled to a carrier, the collection tip comprising hydrophilic and soluble polycaprolactone (PCL) that has been treated with a base having a pH greater than 8 and a neutralizing agent for increasing hydrophilicity, the collection tip being movable from a first protected position within the outer protective housing to a second collecting position outside the outer protective housing, under conditions such that at least a portion of the at least one sample reversibly adheres to the collection tip.

19. The method of claim 18, wherein the at least one sample comprises nucleic acid, and the method further comprises contacting the collection tip and the at least a portion of the at least one sample adhered thereto with a nucleic acid extraction agent resulting in separation of about 51% to about 95% of the nucleic acid from the collection tip.

20. The method of claim 19, wherein the sample is a forensics sample.

21. The method of claim 19, wherein the sample is from a human.

* * * * *